(12) United States Patent
Connolly et al.

(10) Patent No.: US 10,029,267 B2
(45) Date of Patent: Jul. 24, 2018

(54) MULTI-COMPONENT FRAGRANCE DISPENSING APPARATUS

(71) Applicant: The Procter & Gamble Company, Cincinnati, OH (US)

(72) Inventors: William John Cleveland Connolly, Windlesham (GB); Elaine Alice Marie Baxter, London (GB); Neil Charles Dring, Medmenhan (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/354,587

(22) Filed: Nov. 17, 2016

(65) Prior Publication Data
US 2017/0151579 A1 Jun. 1, 2017

Related U.S. Application Data

(60) Provisional application No. 62/260,334, filed on Nov. 27, 2015.

(51) Int. Cl.
*B05B 11/00* (2006.01)
*B01J 13/18* (2006.01)
*B65D 83/68* (2006.01)

(52) U.S. Cl.
CPC .......... *B05B 11/0078* (2013.01); *B01J 13/18* (2013.01); *B65D 83/68* (2013.01)

(58) Field of Classification Search
CPC ....... B05B 11/0078; B65D 83/68; B01J 13/18
See application file for complete search history.

(56) References Cited

U.S. PATENT DOCUMENTS

| 4,428,869 A * | 1/1984 | Munteanu ............... A61K 8/11 512/4 |
| 4,826,048 A | 5/1989 | Skorka et al. |
| 5,967,372 A | 10/1999 | Favre |
| 6,454,135 B1 | 9/2002 | Brozell |
| 7,195,135 B1 * | 3/2007 | Garcia .............. B05B 11/3084 222/137 |
| 7,335,631 B2 | 2/2008 | McDermott et al. |
| 7,524,809 B2 * | 4/2009 | Trinh ................. C11D 3/001 510/101 |
| 7,819,342 B2 | 10/2010 | Spallek et al. |
| 2005/0113282 A1 | 5/2005 | Parekh et al. |

(Continued)

FOREIGN PATENT DOCUMENTS

| EP | 1176945 | 3/2004 |
| GB | 1182520 | 2/1970 |

(Continued)

OTHER PUBLICATIONS

The PCT International Search Report dated Mar. 7, 2017—6 pages.
(Continued)

*Primary Examiner* — Donnell Long

(57) ABSTRACT

The present invention relates to a multi-component fragrance dispensing apparatus comprising at least an aqueous based composition and a volatile solvent based composition, wherein the apparatus comprises two separate containers, two separate non-spray dispensers, and one exit orifice therein. Methods of using the apparatus for providing a longer lasting fragrance is also encompassed by the present invention.

14 Claims, 5 Drawing Sheets

(56) References Cited

U.S. PATENT DOCUMENTS

| | | |
|---|---|---|
| 2005/0226900 A1 | 10/2005 | Brooks et al. |
| 2006/0102656 A1 | 5/2006 | Troost et al. |
| 2006/0205617 A1 | 9/2006 | Holzner et al. |
| 2007/0140042 A1 | 6/2007 | Schanz et al. |
| 2010/0108779 A1* | 5/2010 | Filsouf ............... B05B 11/0054 239/61 |
| 2011/0036867 A1* | 2/2011 | Flores ................. A47K 5/1202 222/144.5 |
| 2011/0152146 A1* | 6/2011 | Denutte .................. A61K 8/11 510/119 |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0279990 A1 | 11/2012 | Werner et al. |
| 2014/0037703 A1 | 2/2014 | Dihora et al. |
| 2014/0193350 A1* | 7/2014 | Bauer .................... A61K 8/347 424/70.11 |
| 2014/0227328 A1 | 8/2014 | Dihora et al. |
| 2015/0071977 A1 | 3/2015 | Dihora et al. |
| 2015/0351519 A1 | 12/2015 | Dring et al. |
| 2015/0352575 A1 | 12/2015 | Dring et al. |
| 2015/0352576 A1 | 12/2015 | Burrowes et al. |
| 2015/0352577 A1 | 12/2015 | Burrowes et al. |
| 2015/0352578 A1 | 12/2015 | Burrowes et al. |
| 2015/0352579 A1 | 12/2015 | Burrowes et al. |
| 2015/0353867 A1 | 12/2015 | Dring et al. |
| 2015/0354550 A1 | 12/2015 | Burrowes et al. |
| 2015/0375245 A1 | 12/2015 | Burrowes et al. |
| 2016/0040104 A1* | 2/2016 | Liu .................... C11D 17/0039 510/296 |
| 2016/0128915 A1* | 5/2016 | Konno ..................... A61Q 5/10 424/62 |
| 2017/0065993 A1 | 3/2017 | Burrowes et al. |
| 2017/0065995 A1 | 3/2017 | Burrowes et al. |
| 2017/0065996 A1 | 3/2017 | Burrowes et al. |
| 2017/0065997 A1 | 3/2017 | Burrowes et al. |
| 2017/0151363 A1 | 6/2017 | Baxter et al. |
| 2017/0151364 A1 | 6/2017 | Baxter et al. |
| 2017/0281480 A1* | 10/2017 | Pringgosusanto ....... A61K 8/11 |
| 2017/0368563 A1 | 12/2017 | Burrowes et al. |

FOREIGN PATENT DOCUMENTS

| | | |
|---|---|---|
| JP | 4464803 | 5/2010 |
| WO | WO 2005018785 | 3/2005 |
| WO | WO2015/191495 | 12/2015 |

OTHER PUBLICATIONS

All Office Actions U.S. Appl. No. 14/734,151.
All Office Actions U.S. Appl. No. 14/734,180.
All Office Actions U.S. Appl. No. 14/734,199.
All Office Actions U.S. Appl. No. 14/734,234.
All Office Actions U.S. Appl. No. 14/734,1348.
All Office Actions U.S. Appl. No. 14/734,429.
All Office Actions U.S. Appl. No. 14/734,462.
All Office Actions U.S. Appl. No. 14/734,512.
All Office Actions U.S. Appl. No. 14/734,588.
All Office Actions U.S. Appl. No. 14/734,673.
Patchan, et al., "Liquid-Filled Metal Microcapsules", ACS Applied Materials & Interfaces, vol. 4, pp. 2406-2412, 2012.
All Office Actions, U.S. Appl. No. 15/354,440.
All Office Actions, U.S. Appl. No. 15/354,533.

* cited by examiner

MULTI-COMPONENT FRAGRANCE DISPENSING APPARATUS

FIELD OF THE INVENTION

The present invention relates to a multi-component fragrance dispensing apparatus and methods for dispensing a dose of an aqueous based composition and a volatile solvent based composition, wherein the aqueous based composition includes microcapsule encapsulated fragrances.

BACKGROUND OF THE INVENTION

Consumers often desire to deliver pleasant fragrances during and/or after application of a product. Such fragrances often contain perfume oils and/or other odoriferous materials that provide a scent for a limited period of time. Certain products, such as fine fragrance products, include a volatile solvent (e.g., ethanol) for solubilizing the perfume oils and/or other odoriferous materials. Unfortunately, the fragrances in these products quickly evaporate and are often noticeable for only a short period of time. One approach to increase the duration of noticeability of a fragrance is to include a controlled-release system into the product. In this regard, microcapsules that encapsulate a fragrance have been used in order to provide for delayed release of the fragrance into the headspace after application. The stability of microcapsules in a composition may be impacted by other ingredients in the composition. For example, volatile solvents like ethanol may cause the microcapsules to be unable to retain their integrity or the encapsulated fragrances to a certain level over time. Therefore, the microcapsules would have to be formulated in a separate composition from the traditional fine fragrance composition comprising the volatile solvents and perfume oils. While dispensers having separate chambers for housing incompatible ingredients/compositions may exist, such dispensers may not be suitable in this case or may not be capable of dispensing certain ingredients/compositions without damaging the microcapsules. Thus, there exists a need for dispensing apparatus that can minimize contact between incompatible ingredients/compositions prior to use and provide longer lasting fragrance to the consumer upon use.

SUMMARY OF THE INVENTION

The present invention is based, in part, on the surprising observation that an aqueous based composition (2) containing microcapsule encapsulated fragrances can be used in combination with a volatile solvent based composition (3), such as for example a more traditional fine fragrance, to impact fragrance longevity. Furthermore, this fragrance longevity is further enhanced by the use of a multi-component fragrance dispensing apparatus (1) having at least two separate containers (10, 20), two separate non-spray dispensers (11, 21), and an exit orifice (30), to minimize mixing of the compositions prior to use. Accordingly, an advantage of the present invention is to provide longer lasting fragrances over time (from compositions dispensed in the multi-component fragrance dispensing apparatus (1) as claimed herein).

One aspect of the invention provides for a multi-component fragrance dispensing apparatus (1) comprising at least an aqueous based composition (2) and a volatile solvent based composition (3), wherein the apparatus (1) comprises: (a) a first container (10) that contains the aqueous based composition (2), and a first non-spray dispenser (11) operably connected to the first container (10), wherein the first non-spray dispenser (11) is in fluid communication with the contained aqueous based composition (2); (b) a second container (20) that contains the volatile solvent based composition (3), and a second non-spray dispenser (21) operably connected to the second container (20), wherein the second non-spray dispenser (21) is in fluid communication with the contained volatile solvent based composition (3); and (c) an exit orifice (30). Preferably, wherein the first non-spray dispenser (11) is in fluid communication with the exit orifice (30) and the second non-spray dispenser (21) is in fluid communication with the exit orifice (30), and wherein the exit orifice (30) dispenses a dose of the aqueous based composition (2) and a dose of the volatile solvent based composition (3). Preferably, wherein the aqueous based composition (2) comprises from about 0.1 wt % to about 95 wt % of water and from about 0.01 wt % to about 50 wt %, preferably from about 1 wt % to about 20 wt %, of a plurality of microcapsules, wherein the wt % is by weight of the total aqueous based composition (2); and the volatile solvent based composition (3) comprises from about 0.01 wt % to about 98 wt %, preferably from about 50 wt % to about 80 wt %, of a volatile solvent and from about 0.01 wt % to about 30 wt %, preferably from about 5 wt % to about 30 wt %, of a first fragrance material, wherein the wt % is by weight of the total volatile solvent based composition (3).

Another aspect of the invention provides for a method of providing a longer lasting fragrance, the method comprises using the aforementioned multi-component fragrance dispensing apparatus (1) as described herein.

BRIEF DESCRIPTION OF THE DRAWINGS

While the specification concludes with the claims particularly pointing out and distinctly claiming the invention, it is believed that the invention will be better understood from the following description of the accompanying figures in which like reference numerals identify like elements, and wherein:

DETAILED DESCRIPTION OF THE INVENTION

Figure 1A:
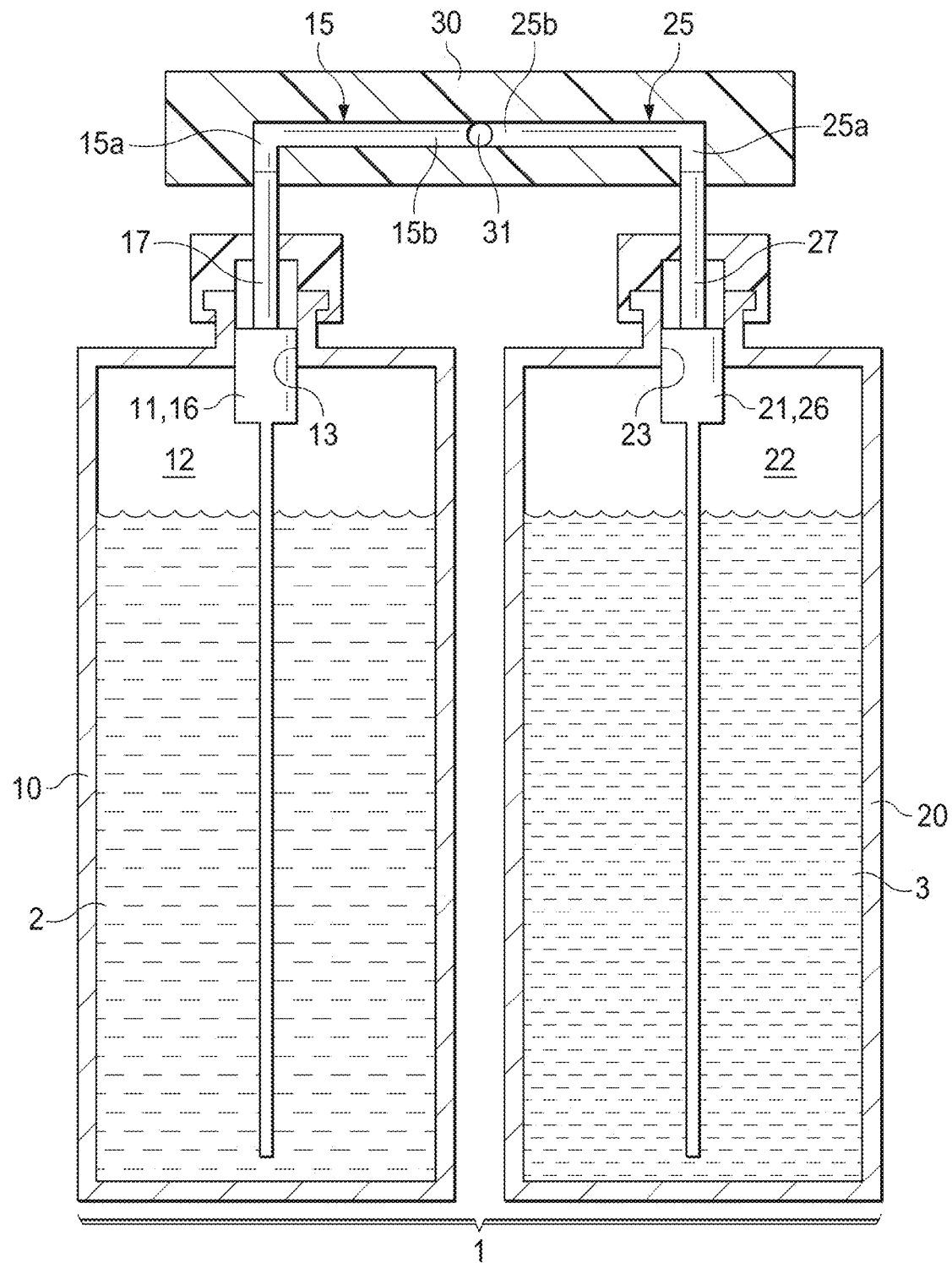
FIG. 1A shows a cross-sectional view of an embodiment of the apparatus (1) according to the present invention.

It is to be understood that the scope of the claims is not limited to the specific devices, apparatuses, methods, conditions or parameters described and/or shown herein, and that the terminology used herein is for the purpose of describing particular embodiments by way of example only and is not intended to be limiting of the claimed invention.

Definitions

Also, as used in the Specification including the appended claims, the articles "a", "an", and "the" mean "one or more."

As used herein, the term "about" when placed before a numerical value "X" refers to an interval extending from 10% of X, preferably 5% of X, and even more preferably to an interval extending from 2% of X.

"Aqueous based composition", as used herein, includes a personal care or cosmetic composition for application to skin or hair, which comprises a fragrance material for the purposes of delivering a pleasant smell to drive consumer acceptance of the personal care or cosmetic composition. Such compositions may also be suitable for application to textiles or any other form of clothing. The personal care or cosmetic compositions can be formulated in a wide variety of products intended for application to the skin and/or hair, such as for non-limiting example: mousses, gels, solids, creams, lotions, ointments, solutions, emulsions, films and combinations thereof. The personal care or cosmetic compositions may be suitable for use as, such as for non-limiting example: hand and body lotions, skin moisturizing products, skin cleansing or disinfecting compositions, foundations, make-up compositions, sun and ultraviolate radiation protection lotions, skin care creams, anti-age preparations, anti-acne preparations, anti-perspirants, conditioners, and other compositions of the similar type. For avoidance of doubt, the term "aqueous based composition" does not include a volatile solvent based composition, such as a fine fragrance composition.

As used herein, any of the terms "comprising", "having", "containing", and "including" means that other parts, steps, etc. which do not adversely affect the end result can be added. Each of these terms encompasses the terms "consisting of" and "consisting essentially of". Unless otherwise specifically stated, the elements and/or equipments herein are believed to be widely available from multiple suppliers and sources around the world.

As used herein, the term "consumer" means both the user of the apparatus and the observer nearby or around the user.

"Dispenser", as used herein, relates to a total system that moves the formulation from the container to the external environment. This may include, such as for example, an exit orifice, connecting pipework, and a system to draw product from the container. "Exit orifice", as used herein, refers to a passage from the dispenser to the external environment. The apparatus according to the present invention includes one exit orifice.

"Fragrance material", as used herein, relates to a perfume raw material ("PRM"), or a mixture of perfume raw materials ("PRMs"), that are used to impart an overall pleasant odour or fragrance profile to a composition. "Fragrance materials" can encompass any suitable perfume raw materials for fragrance uses, including materials such as, for example, alcohols, aldehydes, ketones, esters, ethers, acetates, nitriles, terpene hydrocarbons, nitrogenous or sulfurous heterocyclic compounds and essential oils. However, naturally occurring plant and animal oils and exudates comprising complex mixtures of various chemical components are also know for use as "fragrance materials". The individual perfume raw materials which comprise a known natural oil can be found by reference to Journals commonly used by those skilled in the art such as "Perfume and Flavourist" or "Journal of Essential Oil Research", or listed in reference texts such as the book by S. Arctander, *Perfume and Flavor Chemicals,* 1969, Montclair, N.J., USA and more recently re-published by Allured Publishing Corporation Illinois (1994). Additionally, some perfume raw materials are supplied by the fragrance houses (Firmenich, International Flavors & Fragrances, Givaudan, Symrise) as mixtures in the form of proprietary specialty accords. Non-limiting examples of the fragrance materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

"Essentially free of", as used herein, means that the stated ingredient has not been added to the composition. However, the stated ingredient may incidentally form as a by-product or a reaction product of the other components of the composition.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Situs", as used herein, means the location wherein the composition is applied. Non-limiting examples of a situs include mammalian keratinous tissue and clothing.

"Volatile", as used herein, unless otherwise specified, refers to those materials that are liquid under ambient conditions and which have a measurable vapour pressure at 25° C. These materials typically have a vapor pressure of greater than about 0.0000001 mm Hg ($1.33 \times 10^{-8}$ kPa), alternatively from about 0.02 mm Hg (0.0027 kPa) to about 20 mm Hg (2.7 kPa), and an average boiling point typically less than about 250° C., alternatively less than about 235° C.

All percentages are weight percentages based on the total weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

All temperatures are in Celsius degrees (° C.), unless specifically stated otherwise. All dimensions and values disclosed herein (e.g., quantities, percentages, portions, and proportions) are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Multi-Component Fragrance Dispensing Apparatus

Traditional fine fragrance products include a volatile solvent and fragrance oils. Consumers use these fine fragrance products to deliver pleasant scents to their body and/or clothing. A drawback is that the perceived longevity of the fragrances decreases rapidly over time because the fragrances are typically volatile. However, consumers tend to desire a longer duration of noticeability of the fragrances. As a result, the consumers may have to continually reapply the fine fragrance products after a short period of time in order to keep the fragrance noticeable.

One can increase the duration of noticeability of a fragrance by incorporating a controlled-release system, such as for example, microcapsules encapsulated fragrances, into the product. While microcapsules have existed since the 1950s, there are no known products on the market that contain microcapsules in a composition that also includes a volatile solvent (e.g., ethanol) at levels typically present in fine fragrance products, or that can deliver microcapsules in combination with the volatile solvent (e.g., ethanol). As shown in Table 1, the presence of volatile solvents (e.g., ethanol) in a composition can cause fragrance-loaded microcapsules, such as those whose shells contain a polyacrylate material, to prematurely release the encapsulated fragrance. The loss can be as high as 60% after a five (5) day incubation at room temperature.

TABLE 1

Percent Loss of Encapsulated Fragrance Materials

| Type of Composition | Percentage Leak (%) |
|---|---|
| Ethanol/Water (3:1 ratio) | >60% after 5 days at room temperature |

The problem here is that stability of the microcapsules are impacted by interacting with other ingredients in the composition. For example, the presence of a volatile solvent (e.g., ethanol) in a composition may seriously impact microcapsules. The volatile solvent may reduce the structural/chemical stability of the microcapsules. Additionally, the volatile solvent may also enhance or impair the ability of a fragrance-loaded microcapsule from releasing its encapsulated fragrance into the headspace during use.

Surprisingly, it has been discovered that by minimizing the contact time between the microcapsules and the volatile solvent allows the microcapsules to deliver a noticeable improved fragrance longevity to the consumer. This can be achieved by formulating at least two compositions, wherein at least one composition is aqueous based (2) and contains the microcapsules and a second composition is volatile solvent based (3) and contains the volatile solvent and fragrance material. Although there are known dispensing apparatus that may contain at least two containers to separately house the compositions, they may not deliver a consistent noticeable improved fragrance longevity benefit as described by the present invention. For example, some dispensing apparatus that have more than one container may prematurely mix the microcapsules with the volatile solvent for an excessive duration prior to use, which may lead to damage of the microcapsules themselves. In these situations, the dispensing apparatus may retain a significant amount of a mixture of the mixed compositions somewhere between the dispensers and the containers such that the mixture contains damaged microcapsules. Without wishing to be bound by theory, the damaged microcapsules can cause the fragrance character to be either lost or changed from what was originally designed. When this happens, the overall character of the product is compromised because the leaked fragrance material from the microcapsules can destroy the desirable character of the main fragrance as it was designed.

Specifically, the present invention seeks to overcome this problem and provides for a longer lasting period of noticeability of a fragrance. One aspect of the invention provides a multi-component fragrance dispensing apparatus (1) comprising at least two compositions, specifically an aqueous based composition (2) and a volatile solvent based composition (3). The apparatus (1) may contain three, four or more compositions, as needed, made up of any combinations of the aqueous based and volatile solvent based compositions, according to the desires of the formulator. Accordingly, the apparatus (1) has at least two containers, a first container (10) for storing the aqueous based composition (2) comprising the microcapsules and water, and a second container (20) for storing the volatile solvent based composition (3) comprising the volatile solvent and the first fragrance material. The apparatus may comprise three, four or more containers, corresponding to the number of different compositions that are present. With this design, the apparatus (1) described herein minimizes the contact time between the microcapsules containing composition (2) and the volatile solvent (e.g., ethanol) containing composition (3), allowing the microcapsules to deliver a noticeable longer lasting fragrance to the consumer.

The reduction or avoidance of mixing of the two compositions provides several advantages. First, by keeping the two compositions separate, the apparatus (1) ensures that the carrier (e.g., water) from the aqueous based composition (2) is not intentionally mixed with the volatile solvent based composition (3) during storage or transport to result in a mixture with a lower surface tension than water. As a result, the compositions can be appropriately dispensed during use. Second, by not mixing the two compositions before use, the microcapsules are less likely to have been damaged upon exit from the apparatus (1). Third, by preventing the mixing of the compositions also minimizes and/or eliminates negatives to the main fragrance caused by interaction with the leaked fragrances from the damaged microcapsules.

Furthermore, fine fragrance products typically involves spraying the fine fragrance onto a situs. If a dispenser aerosolizes (i.e., sprays) the microcapsules, then the microcapsules must be more resilient in order to survive intact the various forces (e.g., actuation force) applied to them during spraying. Surprisingly, the inventors discovered that if by avoiding the spraying process of the composition, then the microcapsules do not need to have an increased shell thickness and/or strength in order to survive the travel from the container to the situs without pre-maturely releasing the encapsulated fragrance materials. Accordingly, the apparatus (1) of the present invention overcomes this problem and provides at least two non-spray dispensers (11, 21), preferably separate from each other, for dispensing the two compositions via a single exit orifice (31).

Preferably, the size of the apparatus (1) may be such as to allow it be handheld by the consumers. The apparatus (1) may be any dimensions so long as it is small enough to be portable and conveniently fits into a bag or purse. For example, referring to the embodiments illustrated in FIGS. 1-3, the length×width×depth dimensions of the apparatus (1)

can be in the ranges of: 3-30 cm×1.5-15 cm×0.5-15 cm. It is understood by those skilled in the art that other dimensions are possible without deviating from the present invention. The apparatus (1) can be made of any materials which be molded or shaped, while still being durable enough to hold up to being transported around without breaking. Non-limiting examples include glass, plastic, metal, and combinations thereof. When the apparatus (1) is made of glass, the two containers may be blown from the same piece of molten glass, and may appear as a single container with two separate reservoirs. Alternatively, when the containers are made of glass, the two containers may be blown from separate pieces of molten glass, appears as two containers, each with a single reservoir for storing the contained compositions. One of ordinary skill in the art will appreciate that many possible designs of the containers are possible without deviating from the teachings herein.

Figure 1B:
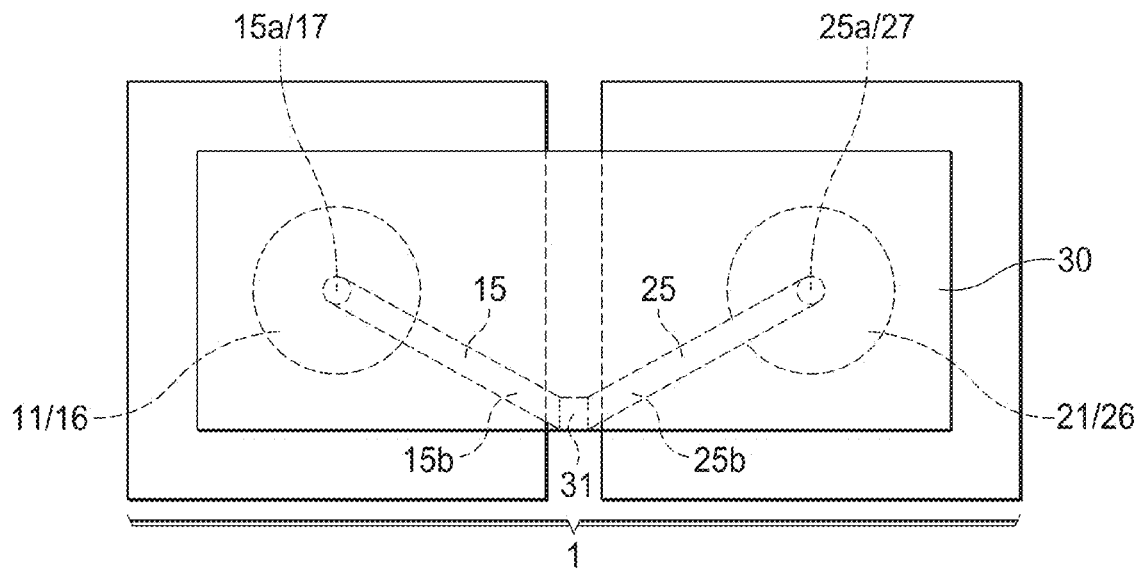
FIG. 1B shows a blown-up top-view of an embodiment of the apparatus (1) showing the flow channels (15, 25) and exit orifice (31) in which contact between the compositions is minimized before dispensing by meeting at the exit orifice (31) without additional mixing areas or system.
Figure 1C:
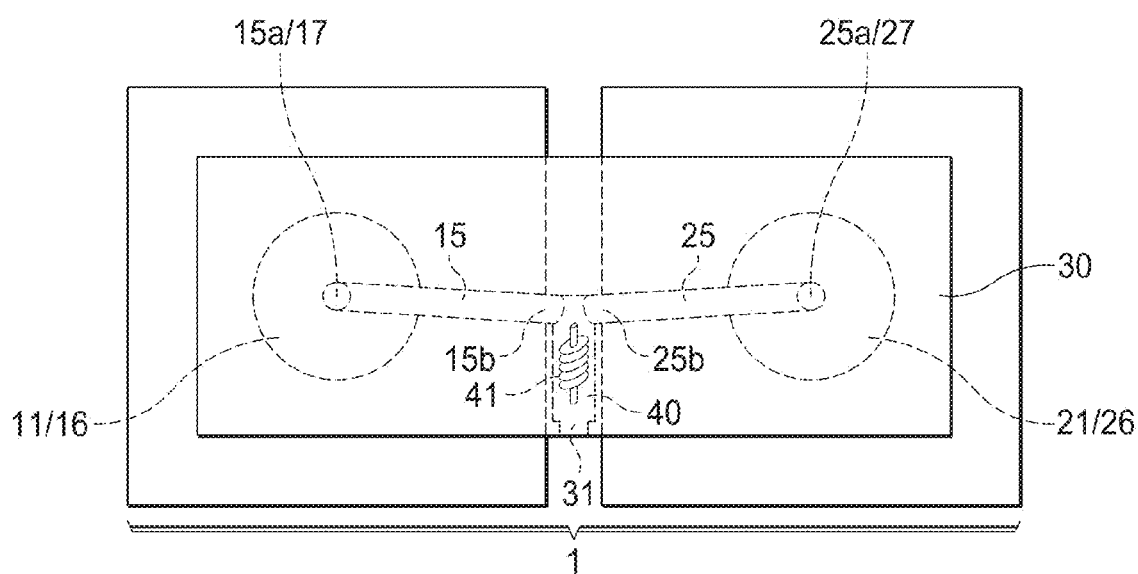
FIG. 1C shows a blown-up top-view of an embodiment of the apparatus (1) showing the flow channels (15, 25) and exit orifice (31) and a mix chamber (40) which includes a static mixer (41). Mixing time will be minimized as the compostions (2, 3) will only mix at this final stage, but for some formulations some mixing may be required to deliver a desirable or homogeneous final product to the situs.

With reference to FIG. 1A, it shows an apparatus (1) which comprises two pump devices, both of which produces a non-spray output. The apparatus (1) comprises a first container (10) and a second container (20). The first container (10) may contain a first reservoir (12) for storing the aqueous based composition (2). The first reservoir (12) may be in fluid communication with a first pump (16) comprising a first piston (17) via which fluid flows into a fluid channel (15). The second container (20) may contain a second reservoir (22) for storing the volatile solvent based composition (3). The second reservoir (22) may be in fluid communication with a second pump (26) comprising a second piston (27) via which fluid flows into a second fluid channel (25). The first and second pistons (17, 27) are in mechanical communication with an actuator (30) and fluid connection via channels (15, 25) with an exit orifice (31) which may or may not be housed within the actuator (30). According to the apparatus (1) in FIG. 1A, the consumer would press the actuator (30) to co-dispense a dose of the aqueous based composition (2) via a first non-spray dispenser (13), such as a finger-pump dispenser (e.g., a VP4 pump from Aptar (Crystal Lake, Ill., USA) when used with a suitable nozzle/orifice such that it does not create a spray, or an Evolux from Aptar), and a dose of the volatile solvent based composition (3) via a second non-spray dispenser (23), such as a pump dispenser (as described for the first non-spray dispenser), through the single exit orifice (31). FIG. 1B shows an apparatus (1) which does not allow for intentional mixing of the two compositions before exiting the apparatus (1). The apparatus (1) may allow for mixing of the aqueous based composition (2) and the volatile solvent based composition (3) upon exiting from the exit orifice (3) either at the situs or on a transfer system (e.g., hands or other application implement and not shown). Alternatively, FIG. 1C, shows an apparatus (1) which optionally includes a mix chamber (40). The mix chamber (40) may include an internal mixing element (41) in the flow path, such as for examples, baffles, apertures, or a helical static mixer. In this case, the apparatus (1) may allow for mixing of the two compositions (2, 3) immediately prior to being co-dispensed through the exit orifice (31). It will be appreciated that the duration of mixing is minimal to avoid and/or minimize any potential damage to the microcapsules from excessive interaction with the volatile solvent.

As shown in FIGS. 1A, 1B, and 1C, the first non-spray dispenser (11) may comprise a first channel (15) having a proximal end (15a) and a distal end (15b); (b) the second non-spray dispenser (21) may comprise a second channel (25) having a proximal end (25a) and a distal end (25b); and (c) optionally, may comprise a mix chamber (40), wherein the mix chamber (40) is in fluid communication with the exit orifice (31). According to this design, the proximal end (15a) of the first channel (15) is in fluid communication with the contained aqueous based composition (2) and the distal end (15b) of the first channel (15) is in fluid communication either with the mix chamber (40) or directly with the exit orifice (31). Further, the proximal end (25a) of the second channel (25) is in fluid communication with the contained volatile solvent based composition (3) and the distal end (25b) of the second channel (25) is in fluid communication either with the mix chamber (40) or directly with the exit orifice (31). These channels (15, 25) may be connected to the compositions (2, 3) either directly via the open ends (13, 23) of the containers (10, 20), or through other aspects of the dispensers (11, 21) (e.g., pump engines and dip tubes).

To minimize damage to the microcapsules, such as may occur when the compositions are forced to flow through the fluid channels (15, 25), the channels (15, 25) may be configured such that one of the channels (15, 25) has a larger diameter than the other. Preferably, the channel with the larger diameter may be used with the aqueous based composition containing the microcapsules to prevent damage to the microcapsules. In some non-limiting examples, such as where the channels (15, 25) are connected to pump devices, they may have a volume of 5 $mm^3$ to 15 $mm^3$, an example of which is when the channels have a volume of 8.4 $mm^3$. Other suitable volumes for these pump-type channels (15, 25) may be 1 $mm^3$ to 100 $mm^3$, although other volumes may be possible. It would be apparent to anyone skilled in the art that the channels (15,25) when connected to other dispenser types (such as shown in FIG. 2) would be of significantly different volumes.

Figure 2:
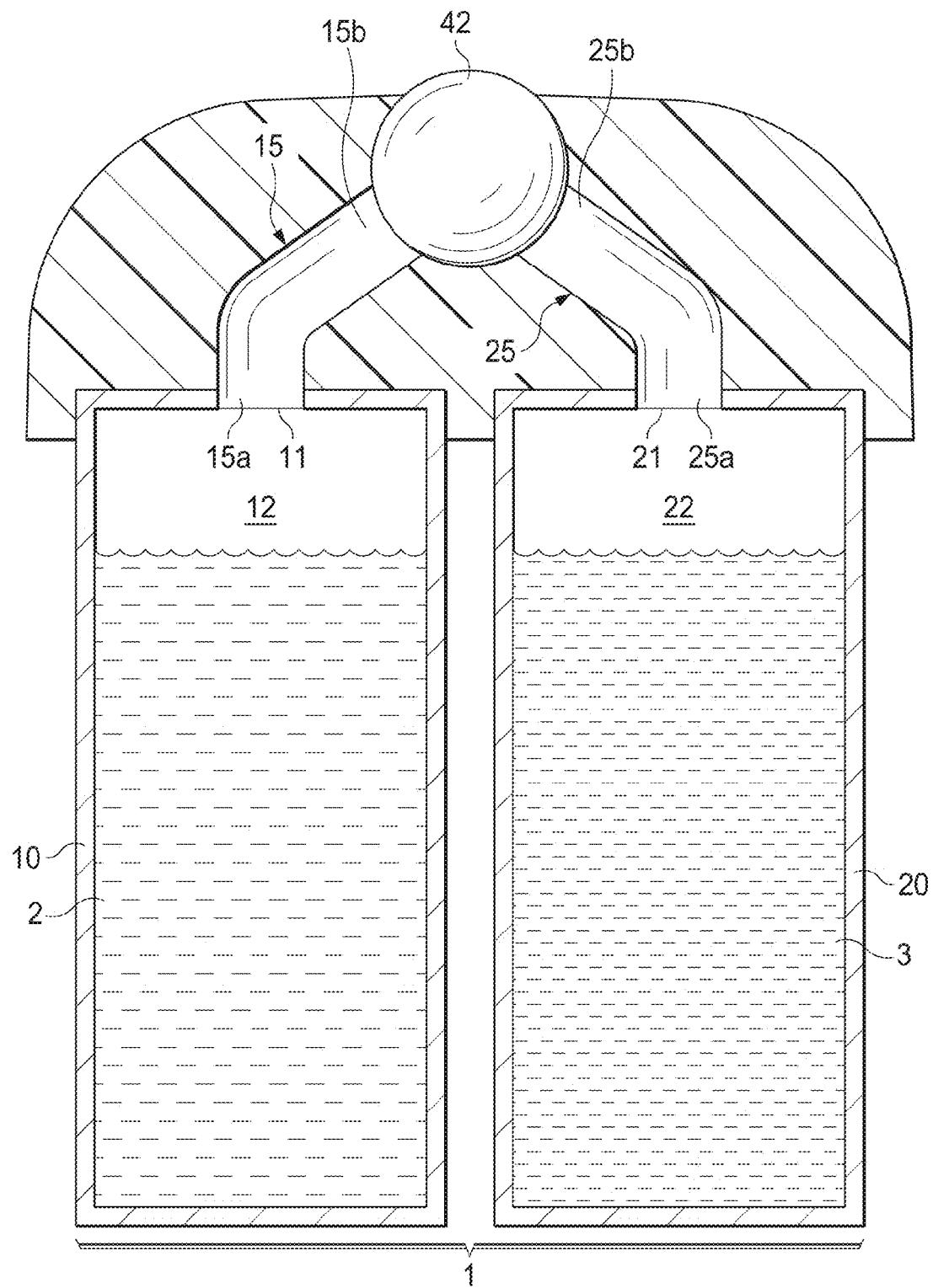
FIG. 2 shows a cross-sectional view of an embodiment of the apparatus (1) according to the present invention.

With continued reference to FIG. 2, the first and second dispensers (11, 21) may be of similar design and functionality. FIG. 2. shows an apparatus (1) in which the two dispensers (11, 21) comprise non-spray dispensers, such as a single roller-ball (42). With this alternate design, the consumer would invert the apparatus (1) so that the roller-ball (42) is immersed in both of the compositions via the respective proximal ends (15a, 25a) of the dispensers (11, 21) and available for co-dispensing by the consumer.

Figure 3:
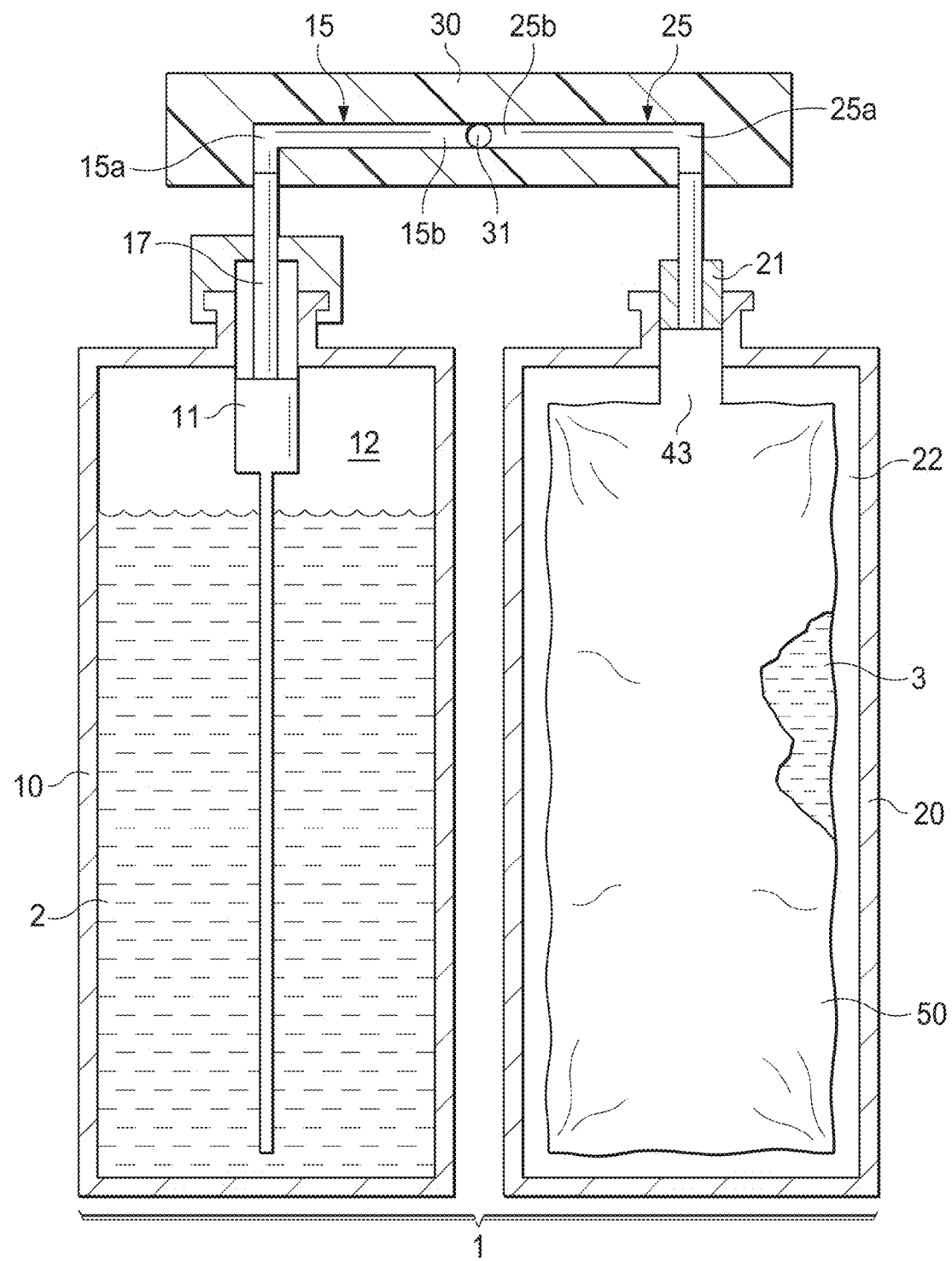
FIG. 3 shows a cross-sectional view of an embodiment of the apparatus (1) according to the present invention.

FIG. 3 shows yet another embodiment of the apparatus (1), wherein the consumer would co-dispense a dose of the aqueous based composition (2) via a first non-spray dispenser (11), such as a finger-pump dispenser (as described for FIG. 1A), and a dose of the volatile solvent based composition (3) via a second non-spray dispenser (21), such as a pressurized bag-in can dispenser (43) (e.g., bag-on-valve from Aptar). With the bag-in-can dispenser (43), the volatile solvent based composition (3) is housed in a bag (50) enclosed within the main reservoir (22). Other possible combinations of non-spray dispensers would be possible without deviating from the scope of the present invention.

With reference to FIGS. 1-3, the apparatus (1) may be configured so that the first dispenser (11) and the second dispenser (21) are adjacent. The reservoirs (12, 22) of the apparatus (1) of the present invention may be of any shape or design. The reservoirs (12, 22) may be of a similar or different size, depending on the volume of each of the composition to be dispensed. For example, the first reservoir (12) may hold a smaller volume than the second reservoir (22) or vice versa. The first reservoir (12) may have an open end (13) and a close end (14) (not shown). The second reservoir (22) may have an open end (23) and a close end (24) (not shown). The open ends (13, 23) are capped or otherwise sealed to prevent leakage of the compositions from the reservoirs (12, 22).

Each of the dispensers (11, 21) is a non-spray dispenser. The non-spray dispenser may be independently selected from: a propellant-driven dispenser (as indicated for spray dispensers, but using a suitable product viscosity to not create a spray, and including foam dispenser nozzles (e.g., iris 02-13 series from Precision)); an aerosol including foaming systems; a roll-on dispenser (e.g., M00013 roller-balls from Baralan (Milan, Italy) or K-009VA from Albea); a dropper (e.g., Serumony from Aptar); a dauber dispenser; a pen dispenser; a brush dispenser (e.g., H/1302-PP from Albea with suitable tip selection); a stick dispenser (e.g. ST048 from Albea); a pipette dispenser (e.g., D/DHE-223 from Albea); a direct application dispenser; a pump dispenser (including finger, trigger, and airless pumps); a bag in can or bottle system (pressurised or not) pump dispenser (as indicated above when combined with suitable product viscosity and nozzle design as to not create a spray); a mechanical/electromechanical dispenser or combinations thereof. The pipette dispenser may include a self-charging pipette. The direct application dispenser may include direct application via open orifice, 1-way valve, or similar control mechanism such as an absorbent or porous material, and via squeezing, shaking, inverting or other suitable mechanism from a bottle, tottle, jar, tube, thermoform, sachet or other container. The pump dispenser may include standard mechanical finger and trigger systems, pump foamers (e.g., F2 from Albea), mechanical, electromechanical and airless systems as indicated for the spray dispensers, but combined with suitable product rheology and nozzle design to not produce a spray. The mechanical/electromechanical dispenser may include a dispenser comprising a mechanical follower activated via twist screw or ratchet (e.g., Exclusive from RPC (Lohne, Germany)).

If the dispensers (11, 21) are of dissimilar types, they must be chosen so that they can both dispense through a single orifice. For example in the case of a roller-ball being chosen, both dispensers (11, 21) must be roller-balls as the ball becomes the orifice, hence a roller-ball for one dispenser cannot be combined with a dropper for the other dispenser, as that would require more than one orifice. Other non-limiting examples of systems that could not be combined to a single orifice include a brush and a pen. In all cases more than one of the above dispensing systems can be combined to form a single dispenser (e.g., a finger-pump delivering the first composition and a bag-in-can delivering the second composition, may both be combined to move the compositions from their respective reservoirs (12, 22) to the final exit orifice which might incorporate a dropper or brush).

The dispensers (11, 21) may be configured to dispense a similar volume ratio (e.g., 1:1) of the aqueous based composition (2) to the volatile solvent based composition (3). Alternatively, the dispensers (11, 21) may be configured to dispense different volume ratios of the aqueous based composition (2) to the volatile solvent based composition (3). In some non-limiting examples, at least the first dispenser (11) may have an output of 5 to 200 µL and the second dispenser (21) may have an output of 5 to 200 µL. The dispensers (11, 21) may be configured to dispense a volume ratio of the volatile solvent based composition (3) to the aqueous based composition (2) at a ratio from 10:1 to 1:10, from 5:1 to 1:5, from 3:1 to 1:3, from 2:1 to 1:2, or even 1:1 or 2:1.

It is to be understood that optional minor improvements such as valves to prevent reverse flow are to be included herein without deviating from the inventions herein. A non-limiting example is a valve included to prevent reverse flow to the channels (15, 25). Other non-limiting minor improvements may include a mesh to prevent agglomerated particles from entering the channels (15, 25).

Compositions

The compositions described herein may include at least two compositions, preferably an aqueous based composition (2) and a volatile solvent based composition (3).

Aqueous Based Composition

Non-limiting examples of the aqueous based composition (2) may include a personal care or cosmetic composition for application to skin or hair, which comprises a fragrance material for the purposes of delivering a pleasant smell to drive consumer acceptance of the personal care or cosmetic composition. Such compositions may also be suitable for application to textiles or any other form of clothing. For avoidance of doubt, the term "aqueous based composition" (2) does not include a volatile solvent based composition (3).

The aqueous based composition (2) may comprise from about 0.1 wt % to about 95 wt %, or from about 5 wt % to 95 wt %, of water, and from about 0.01 wt % to about 50 wt %, from about 1 wt % to about 20 wt %, of a plurality of microcapsules, wherein the wt % is by weight of the total aqueous based composition. The water may function as a carrier. Preferably, the water is USP water. The aqueous based composition (2) herein may include microcapsules. The microcapsules may be any kind of microcapsule disclosed herein or known in the art. The microcapsules may have a shell and a core material encapsulated by the shell.

The shells of the microcapsules may be made from synthetic polymeric materials or naturally-occurring polymers. Synthetic polymers can be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Non-limiting examples of suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; crosslinked silicone fluids; polyamine reacted with polyisocyanates; acrylate monomers polymerized via free radical polymerization, and mixtures thereof. Natural polymers occur in nature and can often be extracted from natural materials. Non-limiting examples of naturally occurring polymers are silk, wool, gelatin, cellulose, proteins, and combinations thereof.

The microcapsules may comprise an oil soluble material that has a C log P of 4.5 or greater, when measured according to the C log P Test Method, preferably the oil soluble material is selected from the group consisting of: mono-, di- and tri-esters of $C_4$-$C_{24}$ fatty acids and glycerine; isopropyl myristate; soybean oil; hexadecanoic acid; methyl ester; isododecane; and combinations thereof.

The microcapsules may be friable microcapsules. A friable microcapsule is configured to release its core material when its shell is ruptured. The rupture can be caused by forces applied to the shell during mechanical interactions. The microcapsules may have a median volume weighted fracture strength of from about 0.1 MPa to about 25.0 MPa, when measured according to the Fracture Strength Test Method, or any incremental value expressed in 0.1 mega Pascals in this range, or any range formed by any of these values for fracture strength. As an example, the microcapsules may have a median volume weighted fracture strength of 0.5-25.0 mega Pascals (MPa), alternatively from 0.5-20.0 mega Pascals (MPa), 0.5-15.0 mega Pascals (MPa), or alternatively from 0.5-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules as described herein.

The microcapsules may have various core material to shell weight ratios. The microcapsules may have a core material to shell ratio that is greater than or equal to: 10% to 90%, 30% to 70%, 50% to 50%, 60% to 40%, 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer can have a total polyacrylate mass, which includes ingredients selected from the group including: amine content 15 of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, the polyacrylate material may form 5-100% of the overall mass, or any integer value for percentage in this range, or any range formed by any of these values for percentage, of the shell. As examples, the polyacrylate material may form at least 5%, at least 10%, at least 25%, at least 33%, at least 50%, at least 70%, or at least 90% of the overall mass of the shell.

The microcapsules may have various shell thicknesses. The microcapsules may have a shell with an overall thickness of 1 to 2000 nanometers, or any integer value for nanometers in this range, or any range formed by any of these values for thickness. As a non-limiting example, the microcapsules may have a shell with an overall thickness of 2 to 1100 nanometers.

The aqueous based composition (2) may comprise of a second fragrance material encapsulated within the microcapsules. The second fragrance material can be the same or different from the first fragrance material that is present in the volatile solvent based composition (3). The first and second fragrance material can be independently selected from a wide range of fragrance materials selected from base, middle and top notes. "Base notes" are characterized by providing animalic, woody, sweet, amber or musky aromas, and not being very volatile. The "middle or heart notes" are associated with desirable aromas such as floral aromas (e.g., jasmin, rose), fruity, marine, aromatic or spicy aromas and have an intermediate volatility. The "top or head notes" provide citrusy, green, light, or fresh aromas, and tend to be highly volatile. The "top or head notes" and "heart or middle notes" tend to evaporate quicker due to their high volatility than "base notes". Therefore, it would be advantageous to include more of the fragrance materials selected from the top, middle and base notes inside the microcapsules to extend the duration of their noticeability.

When the aqueous based composition (2) comprises microcapsules encapsulating a second fragrance material, the aqueous based composition (2) may further include a non-encapsulated fragrance material that may or may not different from the encapsulated second fragrance material. In some preferred examples, the aqueous based composition is essentially free of a material selected from the group consisting of: a propellant; ethanol; a detersive surfactant; and combinations thereof. Non-limiting examples of propellants include: compressed air; nitrogen; inert gases; carbon dioxide; gaseous hydrocarbons like propane, n-butane, isobutene, cyclopropane; and mixtures thereof. Non-limiting examples of detersive surfactants include: non-ionic, anionic, ampholytic, zwitterionic, or cationic surfactants and mixtures thereof.

The aqueous based composition (2) can be formulated in a wide variety of products intended for application to the skin and/or hair, such as, for example: mousses, gels, solids, creams, lotions, ointments, solutions, emulsions, films and combinations thereof. The aqueous based composition may be suitable for use as, such as for example: hand and body lotions, skin moisturizing products, skin cleansing or disinfecting compositions, foundations, make-up compositions, sun and ultraviolate radiation protection lotions, skin care creams, anti-age preparations, anti-acne preparations, antiperspirants, conditioners, and other compositions of the similar type.

Volatile Solvent Based Composition

The volatile solvent based composition (3) may include a fine fragrance composition intended for application to a body surface, such as for example, skin or hair, i.e., to impart a pleasant odour thereto, or cover a malodour thereof. They are generally in the form of perfume concentrates, perfumes, eau de parfums, eau de toilettes, aftershaves, colognes, body splashes, or body sprays. For avoidance of doubt, the term "volatile solvent based composition" (3) does not include an aqueous based composition (2), such as a personal care or cosmetic composition.

The volatile solvent based composition (3) may comprise from about 0.01 wt % to about 98 wt %, preferably from about 50 wt % to about 80 wt %, of a volatile solvent and from about 0.01 wt % to about 30 wt %, preferably from about 5 wt % to about 30 wt %, of a first fragrance material, wherein the wt % is by weight of the total volatile solvent based composition (3). Preferably, the volatile solvent is a branched or unbranched $C_1$ to $C_{10}$ alkanyl, alkenyl or alkynyl having at least one alcohol moiety, preferably ethanol, isopropanol, or glycol. The first fragrance material may be selected from a wide variety of chemicals such as for non-limiting examples alcohols, aldehydes, ketones, ethers, Schiff bases, nitriles, and esters.

More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the individual fragrance materials may be about −0.5 or greater. As used herein, "C log P" means the logarithm to the base 10 of the octanol/water partition coefficient. The C log P can be readily calculated from a program called "C LOG P" which is available from Daylight Chemical Information Systems Inc., Irvine Calif., USA or calculated using Advanced Chemistry Development (ACD/Labs) Software V 2015 (or latest version update). Octanol/water partition coefficients are described in more detail in U.S. Pat. No. 5,578,563.

Additional Ingredients

The aqueous based (2) and volatile solvent based compositions (3) described herein may include a suspending agent, a coloring agent, surfactants, emollients, preservatives or mixtures thereof. Non-limiting examples of suitable suspending agents and coloring agents are disclosed in U.S. Patent Publication No. US2015/071977 (Procter & Gamble).

Method of Use

In another aspect, the present invention is directed to a method of providing a longer lasting fragrance. The method comprises the provision of a multi-component fragrance dispensing apparatus (1) according to the invention. The method further comprises the steps of dispensing a dose of an aqueous based composition (2) to a situs; and dispensing a dose of a volatile solvent based composition (3) to the situs; wherein the aqueous based composition (2) and the volatile based composition (3) are dispensed simulataneously or sequentially, in either order. The apparatus (1) may dispense a dose of the aqueous based composition (2) and a dose of the volatile solvent based composition (3) such that they have a combined volume of from 2 mL to 300 mL, or alternatively from 10 mL to 140 mL, or alternatively from 20 mL to 100 mL. The present invention is also directed to the use of a multi-component fragrance dispensing apparatus (1) for providing a longer lasting fragrance.

The compositions disclosed herein may be applied to one or more skin surfaces and/or one or more mammalian keratinous tissue surfaces as part of a user's daily routine or regimen. Additionally or alternatively, the compositions herein may be used on an "as needed" basis. The compositions may also be applied to any article, such as a textile. For example, while the combinations of the apparatus (1) and compositions described herein are exquisitely designed to be used as a fine fragrance spray, it is understood that such combinations may also be used as a body spray, feminine spray, or other spray. The size, shape, and aesthetic design of the apparatus described herein may vary widely to suit the end usage.

The present invention also provides kits that contain the apparatus (1) of the invention. The kit also includes instructions for use of the apparatus (1) for providing to the consumers longer lasting fragrance.

Test Methods

The following assays set forth must be used in order that the invention described and claimed herein may be more fully understood.

Test Method 1: Fracture Strength of Microcapsules

One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in de-ionized (DI) water to form a slurry for characterization. It is to be understood that the fracture strength of microcapsules extracted from a finished product may vary +/−15% from the ranges described herein as the finished product may alter the microcapsules' fracture strength over time.

To calculate the percentage of microcapsules which fall within a claimed range of fracture strengths, three different measurements are made and two resulting graphs are utilized. The three separate measurements are namely: i) the volume-weighted particle size distribution (PSD) of the microcapsules; ii) the diameter of at least 10 individual microcapsules within each of 3 specified size ranges, and; iii) the rupture-force of those same 30 or more individual microcapsules. The two graphs created are namely: a plot of the volume-weighted particle size distribution data collected at i) above; and a plot of the modeled distribution of the relationship between microcapsule diameter and fracture-strength, derived from the data collected at ii) and iii) above. The modelled relationship plot enables the microcapsules within a claimed strength range to be identified as a specific region under the volume-weighted PSD curve, and then calculated as a percentage of the total area under the curve.

a.) The volume-weighted particle size distribution (PSD) of the microcapsules is determined via single-particle optical sensing (SPOS), also called optical particle counting (OPC), using the AccuSizer 780 AD instrument, or equivalent, and the accompanying software CW788 version 1.82 (Particle Sizing Systems, Santa Barbara, Calif., U.S.A.). The instrument is configured with the following conditions and selections: Flow Rate=1 mL/sec; Lower Size Threshold=0.50 µm; Sensor Model Number=LE400-05SE; Autodilution=On; Collection time=120 secs; Number channels=512; Vessel fluid volume=50 mL; Max coincidence=9200. The measurement is initiated by putting the sensor into a cold state by flushing with water until background counts are less than 100. A sample of microcapsules in suspension is introduced, and its density of particles is adjusted with DI water as necessary via autodilution to result in particle counts of at least 9200 per mL. During a time period of 120 secs the suspension is analyzed. The resulting volume-weighted PSD data are plotted and recorded, and the values of the mean, $10^{th}$ percentile, and $90^{th}$ percentile are determined.

b.) The diameter and the rupture-force value (also known as the bursting-force value) of individual microcapsules are measured via a computer-controlled micromanipulation instrument system which possesses lenses and cameras able to image the microcapsules, and which possesses a fine, flat-ended probe connected to a force-transducer (such as the Model 403A available from Aurora Scientific Inc, Canada, or equivalent), as described in: Zhang, Z. et al. (1999) "Mechanical strength of single microcapsules determined by a novel micromanipulation technique." *J. Microencapsulation*, vol. 16, no. 1, pages 117-124, and in: Sun, G. and Zhang, Z. (2001) "Mechanical Properties of Melamine-Formaldehyde microcapsules." *J. Microencapsulation*, vol. 18, no. 5, pages 593-602, and as available at the University of Birmingham, Edgbaston, Birmingham, UK.

c.) A drop of the microcapsule suspension is placed onto a glass microscope slide, and dried under ambient conditions for several minutes to remove the water and achieve a sparse, single layer of solitary particles on the dry slide. Adjust the concentration of microcapsules in the suspension as needed to achieve a suitable particle density on the slide. More than one slide preparation may be needed.

d.) The slide is then placed on a sample-holding stage of the micromanipulation instrument. Thirty or more microcapsules on the slide(s) are selected for measurement, such that there are at least ten microcapsules selected within each of three pre-determined size bands. Each size band refers to the diameter of the microcapsules as derived from the Accusizer-generated volume-weighted PSD. The three size bands of particles are: the Mean Diameter +/−2 µm; the $10^{th}$ Percentile Diameter +/−2 µm; and the $90^{th}$ Percentile Diameter +/−2 µm. Microcapsules which appear deflated, leaking or damaged are excluded from the selection process and are not measured.

e.) For each of the 30 selected microcapsules, the diameter of the microcapsule is measured from the image on the micromanipulator and recorded. That same microcapsule is then compressed between two flat surfaces, namely the flat-ended force probe and the glass microscope slide, at a speed of 2 µm per sec, until the microcapsule is ruptured. During the compression step, the probe force is continuously measured and recorded by the data acquisition system of the micromanipulation instrument.

f.) The cross-sectional area is calculated for each of the selected microcapsules, using the diameter measured and assuming a spherical particle ($\pi r2$, where r is the radius of the particle before compression). The rupture force is determined for each selected particle from the recorded force probe measurements, as demonstrated in Zhang, Z. et al. (1999) "Mechanical strength of single microcapsules determined by a novel micromanipulation technique." *J. Microencapsulation*, vol. 16, no. 1, pages 117-124, and in: Sun, G. and Zhang Z. (2001) "Mechanical Properties of Melamine-Formaldehyde microcapsules." *J. Microencapsulation*, vol. 18, no. 5, pages 593-602.

g.) The Fracture Strength of each of the 30 or more microcapsules is calculated by dividing the rupture force (in Newtons) by the calculated cross-sectional area of the respective microcapsule.

h.) On a plot of microcapsule diameter versus fracture-strength, a Power Regression trend-line is fit against all 30 or more raw data points, to create a modeled distribution of the relationship between microcapsule diameter and fracture-strength.

i.) The percentage of microcapsules which have a fracture strength value within a specific strength range is determined by viewing the modeled relationship plot to locate where the curve intersects the relevant fracture-strength limits, then reading off the microcapsule size limits corresponding with those strength limits. These microcapsule size limits are then located on the volume-weighted PSD plot and thus identify an area under the PSD curve which corresponds to the portion of microcapsules falling within the specified strength range.

The identified area under the PSD curve is then calculated as a percentage of the total area under the PSD curve. This percentage indicates the percentage of microcapsules falling with the specified range of fracture strengths.

Test Method 2: C Log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and c. A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A. or calculated using Advanced Chemistry Development (ACD/Labs) Software Version 2015 (or latest version update).

Test Method 3: Boiling Point

Boiling point is measured by ASTM method D2887-04a, "Standard Test Method for Boiling Range Distribution of Petroleum Fractions by Gas Chromatography," ASTM International.

Test Method 4: Volume Weight Fractions

Volume weight fractions are determined via the method of single-particle optical sensing (SPOS), also called optical particle counting (OPC). Volume weight fractions are determined via an AccuSizer 780/AD supplied by Particle Sizing Systems of Santa Barbara Calif., U.S.A. or equivalent.

Procedure:

1) Put the sensor in a cold state by flushing water through the sensor.
2) Confirm background counts are less than 100 (if more than 100, continue the flush).
3) Prepare particle standard: pipette approx. 1 mL of shaken particles into a blender filled with approx. 2 cups of DI water. Blend it. Pipette approx. 1 mL of diluted, blended particles into 50 mL of DI water.
4) Measure particle standard: pipette approx. 1 mL of double diluted standard into Accusizer bulb. Press the start measurement-Autodilution button. Confirm particles counts are more than 9200 by looking in the status bar. If counts are less than 9200, press stop and inject more sample(s).
5) Immediately after measurement, inject one full pipette of soap (5% Micro 90) into bulb and press the Start Automatic Flush Cycles button.

Test Method 5: Determining Median Volume-Weighted Particle Size of Microcapsules One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.

The median volume-weighted particle size of the microcapsules is measured using an Accusizer 780A, made by Particle Sizing Systems, Santa Barbara Calif., or equivalent. The instrument is calibrated from 0 to 300 µm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The accusizer should be reading in excess of 9200 counts/sec. If the counts are less than 9200, then add additional sample(s). Dilute the test sample until 9200 counts/second then the evaluation should be initiated. After 2 mins of testing, the Accusizer will display the results, including the median volume-weighted particle size.

Test Method 6: Fragrance Intensity Test

In order to show the effect of microcapsule encapsulated fragrances in the aqueous based composition in the presence of a secondary EdT phase in the volatile solvent based composition on the intensity of the fragrance profile, test compositions are made as described in the Example section, and given to panelists to evaluate in multiple delivery forms. The possible delivery forms as follows:

| Group | Treatment | Dispenser |
|---|---|---|
| A | Volatile solvent based composition + Aqueous based composition | Volatile solvent based composition via non-spray dispenser[a] and aqueous based composition via non-spray dispenser[b] simultaneously |

[a]Example of standard spray dispenser include the VP4 pump from Aptar Beauty, Sinfonia ® pump from Westrock or SP22+ from Albea and incorporating a suitable spray nozzle/actuator (e.g., NS60 for the Aptar pump).
[b]Example of standard non-spray dispenser includes glass bottle and M00013 roller-ball from Baralan S.p.A. (Milan, Italy) or VP4 pump from Aptar Beauty (United States), Sinfonia ® pump from Westrock (Virgina, United States) or SP22+ from Albea (Florida, United States).

At the testing facility, 70 µL samples of the control EdT phase in the volatile solvent based composition is applied to a glass slide and placed on a hot plate at 32° C. to represent skin temperature for varying durations. At the same time, 70 µL samples of the EdT phase in the volatile solvent based composition and 50 µL samples of the microcapsule encapsulated fragrances in the aqueous based composition are applied to glass slides as per the combination above. It is important that glass slides of samples that are to be later compared are prepared at the same time. The panelists are asked to evaluate the perceived fragrance intensity of each glass slide sample versus the control at given time point, both before and after rubbing the slide. Rubbing mechanically breaks the microcapsules, releasing fresh perfume oil and increasing fragrance intensity. This reflects the experience that a consumer would have when using a combined EdT/microcapsule product, whereby movement would result in rubbing of the applied product on the skin.

In this test, rubbing is done by the panelists with their finger. A fresh nitrile cot is placed on the finger for each slide and the panelists rub from left to right to left across the whole slide twice, i.e., four movements. Slides are presented coded so that their identity is not known by the panelists. Within a given time point panelists evaluate the slides in a random order and are able to revisit their assessment as they work through the slides at that time point. All pre-rub assessments are completed before moving on to the post-rub assessments. Their assessments are recorded. In the subsequent analysis, the data for intensity are drawn from the independent assessments carried out at a given time point. Panelists are selected from individuals who are either trained to evaluate fragrances according to the scales below or who have experience of fragrance evaluation in the industry. Typically, around 10 panelists are used to evaluate a given product and its control.

(a) Fragrance Intensity:

The panelists are asked to give a score on a scale of 0 to 5 for perceived fragrance intensity versus the control (which is set at 0) pre- and post-rub according to the odour intensity scale set out in Table 2 below.

TABLE 2

Odour Intensity Scale

| Score | Fragrance Intensity |
|---|---|
| 0 | None |
| 1 | Very Weak |
| 2 | Weak |
| 3 | Moderate |
| 4 | Strong |
| 5 | Very Strong |

In table 2 above a score of 1 indicates a very weak increase of intensity in comparison to the control and a score of 5 indicates a very strong increase of intensity in comparison to the control.

The results of the panelists are averaged and then analysed using Analysis of Variance methods. The model treats the subject as a random effect and looks at the impact of product delivery method and time. From the analysis the least square means for the product delivery method and time interaction are obtained. These means (as well as their confidence intervals) are then plotted to enable comparisons between product delivery methods at each time point, pre and post rub. It should be noted that the confidence levels plotted are intended as a guide, and not as a statistical comparison, as they do not take into account that multiple testing has been performed. As well as a graphical assessment, statistical comparisons between the product delivery methods at each of the time points are performed. The p-values for the product delivery method differences are obtained, with p-values $<0.05$ indicating a statistical difference between the two products at 5% significance (or 95% confidence).

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Example 1: Polyacrylate Microcapsule

An oil solution, consisting of 128.4 g fragrance oil, 32.1 g isopropyl myristate, 0.86 g DuPont Vazo™-67, and 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 mins, held at 75° C. for 45 mins, and cooled to 50° C. in 75 mins. This will be called oil solution A.

In a reactor vessel, an aqueous solution is prepared consisting of 300 g deionized water to which is dispersed 2.40 g of Celvol™ 540 polyvinyl alcohol at 25° C. The mixture is heated to 85° C. and held there for 45 mins. The solution is cooled to 30° C. 1.03 g of Wako Chemicals V-501 initiator is added, along with 0.51 g of 40% sodium hydroxide solution. Heat the solution to 50° C., and maintain the solution at that temperature.

To the oil solution A, add 0.19 g of tert-butyl amino ethyl methacrylate (Sigma Aldrich), 0.19 g of beta-carboxy ethyl acrylate (Sigma Aldrich), and 15.41 g of Sartomer CN975 (Sartomer, Inc.). Mix the acrylate monomers into the oil phase for 10 mins. This will be called oil solution B. Use a Caframo™ mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 mins to emulsify the oil phase into the water solution. After milling is completed, mixing is continued with a 3" propeller at 350 rpm. The batch is held at 50° C. for 45 mins, the temperature is increased to 75° C.

in 30 mins, held at 75° C. for 4 hrs, heated to 95° C. in 30 mins and held at 95° C. for 6 hrs. The batch is then allowed to cool to room temperature.

The resultant microcapsules have a median particle size of 12.6 microns, a fracture strength of 7.68±2.0 MPa, and a 51%±20% deformation at fracture.

Example 2: Polyacrylate Microcapsules

An oil solution, consisting of 96 g fragrance oil, 64 g isopropyl myristate, 0.86 g DuPont Vazo™-67, and 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 mins, held at 75° C. for 45 mins, and cooled to 50° C. in 75 mins. This will be called oil solution A.

In a reactor vessel, an aqueous solution is prepared consisting of 300 g deionized water to which is dispersed 2.40 grams of Celvol™ 540 polyvinyl alcohol at 25° C. The mixture is heated to 85° C. and held there for 45 mins. The solution is cooled to 30° C. 1.03 g of Wako Chemicals V-501 initiator is added, along with 0.51 g of 40% sodium hydroxide solution. Heat the solution to 50° C., and maintain the solution at that temperature.

To the oil solution A, add 0.19 g of tert-butyl amino ethyl methacrylate (Sigma Aldrich), 0.19 g of beta-carboxy ethyl acrylate (Sigma Aldrich), and 15.41 g of Sartomer CN975 (Sartomer, Inc.). Mix the acrylate monomers into the oil phase for 10 mins. This will be called oil solution B. Use a Caframo™ mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 mins to emulsify the oil phase into the water solution. After milling is completed, mixing is continued with a 3" propeller at 350 rpm. The batch is held at 50° C. for 45 mins, the temperature is increased to 75° C. in 30 mins, held at 75° C. for 4 hrs, heated to 95° C. in 30 mins and held at 95° C. for 6 hrs. The batch is then allowed to cool to room temperature.

The resultant microcapsules have a median particle size of 12.6 microns, a fracture strength of 2.60±1.2 MPa, 37%±15% deformation at fracture.

Example 3: Polyacrylate Microcapsules

An oil solution, consisting of 128.4 g fragrance oil, 32.1 g isopropyl myristate, 0.86 g DuPont Vazo™-67, and 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 mins, held at 75° C. for 45 mins, and cooled to 50° C. in 75 mins. This will be called oil solution A.

In a reactor vessel, an aqueous solution is prepared consisting of 300 g deionized water to which is dispersed 2.40 g of Celvol™ 540 polyvinyl alcohol at 25° C. The mixture is heated to 85° C. and held there for 45 mins. The solution is cooled to 30° C. 1.03 g of Wako Chemicals V-501 initiator is added, along with 0.51 g of 40% sodium hydroxide solution. Heat the solution to 50° C., and maintain the solution at that temperature.

To the oil solution A, add 0.19 g of tert-butyl amino ethyl methacrylate (Sigma Aldrich), 0.19 g of beta-carboxy ethyl acrylate (Sigma Aldrich), and 15.41 g of Sartomer CN975 (Sartomer, Inc.). Mix the acrylate monomers into the oil phase for 10 mins. This will be called oil solution B. Use a Caframo™ mixer with a 4-blade pitched turbine agitator.

Start nitrogen blanket on top of the aqueous solution in reactor. Start transferring the oil solution B into the aqueous solution in the reactor, with minimal mixing. Increase mixing to 1300-1600 rpm, for 60 mins to emulsify the oil phase into the water solution. After milling is completed, mixing is continued with a 3" propeller at 350 rpm. The batch is held at 50° C. for 45 mins, the temperature is increased to 75° C. in 30 mins, held at 75° C. for 4 hrs, heated to 95° C. in 30 mins and held at 95° C. for 6 hrs. The batch is then allowed to cool to room temperature.

The resultant microcapsules have a median particle size of 26.1 microns, a fracture strength of 1.94±1.2 MPa, 30%±14% deformation at fracture.

Example 4: Polyacrylate Microcapsules

An oil solution, consisting of 128.4 g fragrance oil, 32.1 g isopropyl myristate, 0.86 g DuPont Vazo™-67, and 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 mins, held at 75° C. for 45 mins, and cooled to 50° C. in 75 mins. This will be called oil solution A.

In a reactor vessel, an aqueous solution is prepared consisting of 300 g deionized water to which is dispersed 2.40 g of Celvol™ 540 polyvinyl alcohol at 25° C. The mixture is heated to 85° C. and held there for 45 mins. The solution is cooled to 30° C. 1.03 g of Wako Chemicals V-501 initiator is added, along with 0.51 g of 40% sodium hydroxide solution. Heat the solution to 50° C., and maintain the solution at that temperature.

To the oil solution A, add 0.19 g of tert-butyl amino ethyl methacrylate (Sigma Aldrich), 0.19 g of beta-carboxy ethyl acrylate (Sigma Aldrich), and 15.41 g of Sartomer CN975 (Sartomer, Inc.). Mix the acrylate monomers into the oil phase for 10 mins. This will be called oil solution B. Use a Caframo™ mixer with a 4-blade pitched turbine agitator.

Start nitrogen blanket on top of the aqueous solution in reactor. Start transferring the oil solution B into the aqueous solution in the reactor, with minimal mixing. Increase mixing to 2500-2800 rpm, for 60 mins to emulsify the oil phase into the water solution. After milling is completed, mixing is continued with a 3" propeller at 350 rpm. The batch is held at 50° C. for 45 mins, the temperature is increased to 75° C. in 30 mins, held at 75° C. for 4 hrs, heated to 95° C. in 30 mins and held at 95° C. for 6 hrs. The batch is then allowed to cool to room temperature.

The resultant microcapsules have a median particle size of 10.0 microns, a fracture strength of 7.64±2.2 MPa, 56%±20% deformation at fracture.

Example 5: Polyurea/urethane Microcapsules

An aqueous solution, consisting of 6.06 g Celvol™ 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hrs, and allowed to cool to room temperature. The median particle size of the resultant microcapsules is 10 microns.

Example 6: Polyurea/Urethane Microcapsules

Prepare the Oil Phase by adding 4.44 g of isophorone diisocyanate (Sigma Aldrich) to 5.69 g of Scent A fragrance oil. Prepare a Water Phase by mixing 1.67 g of Ethylene Diamine (Sigma Aldrich) and 0.04 g of 1,4-Diazabicyclo[2.2.2]octane (Sigma Aldrich) into 40 g of a 5 wt % aqueous solution of Polyvinylpyrrolidone K-90 (Sigma Aldrich) at 10° C. Next, add the Oil Phase contents to 15.0 g of a 5 wt % aqueous solution of Polyvinylpyrrolidone K-90 (Sigma Aldrich), while agitating the mix at 1400 rpm using a Janke & Kunkel IKA® Laboretechnik RW20 DZM motor with a 3-blade turbine agitator for approximately 9 mins Next, add the addition of the Water Phase into the emulsified Oil Phase dropwise over 6.5 mins, while continuing to agitate at 1400 rpm. Continue to agitate for 23 mins, then reduce the agitation speed to 1000 rpm. After 3.75 additional hrs, reduce the agitation speed to 500 rpm, and continue to agitate for 14 hrs. Start heating the dispersion to 50° C., for 2 hrs. Age the capsules at 50° C. for 2 hours, then collect the microcapsules. The resultant microcapsules have a median particle size of 12 microns.

Example 7: Polyacrylate Microcapsules

The polyacrylate microcapsule may be prepared as follows. An oil solution, consisting of 112.34 g fragrance oil, 12.46 g isopropyl myristate, 2.57 g DuPont Vazo™-67, and 2.06 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 mins, held at 75° C. for 45 mins, and cooled to 50° C. in 75 mins. This will be called oil solution A.

In a reactor vessel, an aqueous solution is prepared consisting of 300 g deionized water to which is dispersed 2.40 g of Celvol™ 540 polyvinyl alcohol at 25° C. The mixture is heated to 85° C. and held there for 45 mins. The solution is cooled to 30° C. 1.03 g of Wako Chemicals V-501 initiator is added, along with 0.51 g of 40% sodium hydroxide solution. Heat the solution to 50° C., and maintain the solution at that temperature.

To the oil solution A, add 0.56 g of tert-butyl amino ethyl methacrylate (Sigma Aldrich), 0.56 g of beta-carboxy ethyl acrylate (Sigma Aldrich), and 46.23 g of Sartomer CN975 (Sartomer, Inc.). Mix the acrylate monomers into the oil phase for 10 mins. This will be called oil solution B. Use a Caframo™ mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 mins to emulsify the oil phase into the water solution. After milling is completed, mixing is continued with a 3" propeller at 350 rpm. The batch is held at 50° C. for 45 mins, the temperature is increased to 75° C. in 30 mins, held at 75° C. for 4 hrs, heated to 95° C. in 30 mins and held at 95° C. for 6 hrs. The batch is then allowed to cool to room temperature.

Example 8: Spray Drying of Perfume Microcapsules

The microcapsules of Example 1 are pumped at a rate of 1 Kg/hr into a co-current spray dryer (Niro Production Minor, 1.2 meter diameter) and atomized using a centrifugal wheel (100 mm diameter) rotating at 18,000 rpm. Dryer operating conditions are: air flow of 80 Kg/hr, an inlet air temperature of 200° C., an outlet temperature of 100° C., dryer operating at a pressure of −150 mm Hg of water vacuum. The dried powder is collected at the bottom of a cyclone. The collected microcapsules have an approximate particle diameter of 11 microns. The equipment used the spray drying process may be obtained from the following suppliers: IKA® Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 9: Exemplary Compositions

The apparatus according to the present invention may comprise at least one aqueous based composition and one volatile solvent based composition as provided in the tables below at the indicated percentages.

TABLE 3

Aqueous Based Composition

| Ingredients | (% w/w) |
|---|---|
| Water | 92.5847 |
| Microcapsules (from Examples 1-8) | 6.0361 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |
| Polyvinyl alcohol | 0.0655 |
| Sodium Benzoate | 0.0409 |
| Potassium Sorbate | 0.0409 |
| Xanthan Gum | 0.0246 |

TABLE 4

Volatile Solvent Based Composition

| Ingredients | (% w/w) |
|---|---|
| Ethanol (96%) | 74.88 |
| Fragrance material | 14 |
| Water | 10.82 |
| Diethylamino Hydroxybenzol Hexyl Benzoate | 0.195 |
| Ethylhexyl Methoxycinnamate | 0.105 |

Example 10: Fragrance Intensity Test

Compositions disclosed in Tables 3 and 4 are applied to glass slides in accordance with the protocol described in Method Section and a panel of 10 panelists evaluated the perceived fragrance intensity at initial time 0, then at various time points, typically 1 hour, 2 hours, 4 hours and 8 hours post application, pre- and post-rubbing. Panelists are asked to score the compositions for the longevity and/or fidelity of the fragrance profile on a scale of 0 to 5, wherein 0 represents a no fragrance is detected and 5 represents a very strong fragrance intensity is detected. The results of the panelists are then averaged and discussed below.

The p-values obtained for the product delivery method, pre- and post-rubbing, are detailed below in Table 5.

TABLE 5

| P-values | |
|---|---|
| Non-Spray EdT and Non-Spray PMC (Simultaneously) | |
| Pre-Rubbing | 0.15455 |
| Post-Rubbing | 0.0000 |

Figure 4A:
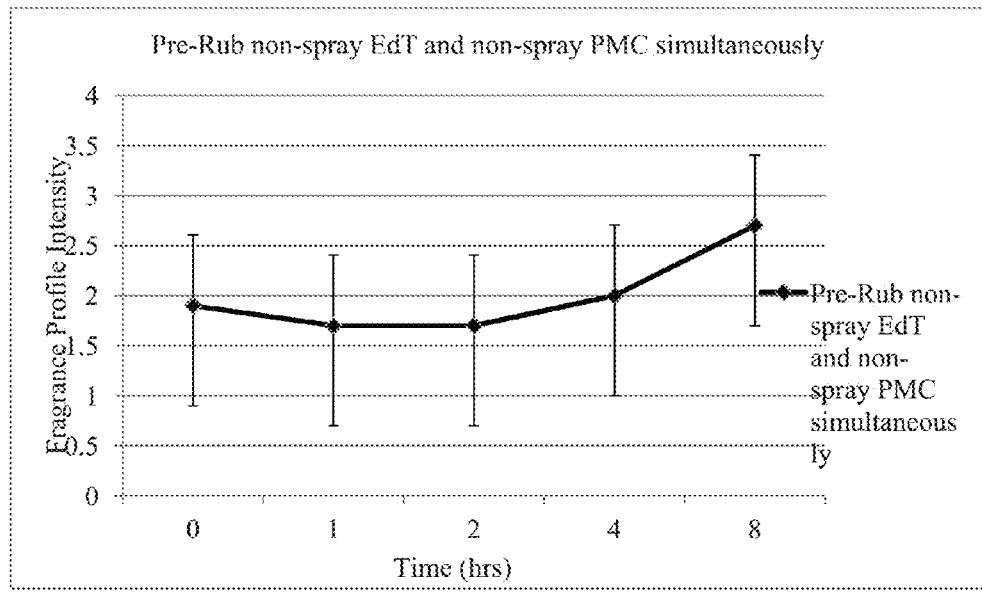
FIG. 4a shows the panel test results of perceived fragrance intensity profile of a volatile solvent based composition via non-spray dispenser and an aqueous based composition via non-spray dispenser simultaneously, as compared to a control, and as a function of time elapsed since application pre-rubbing.
Figure 4B:
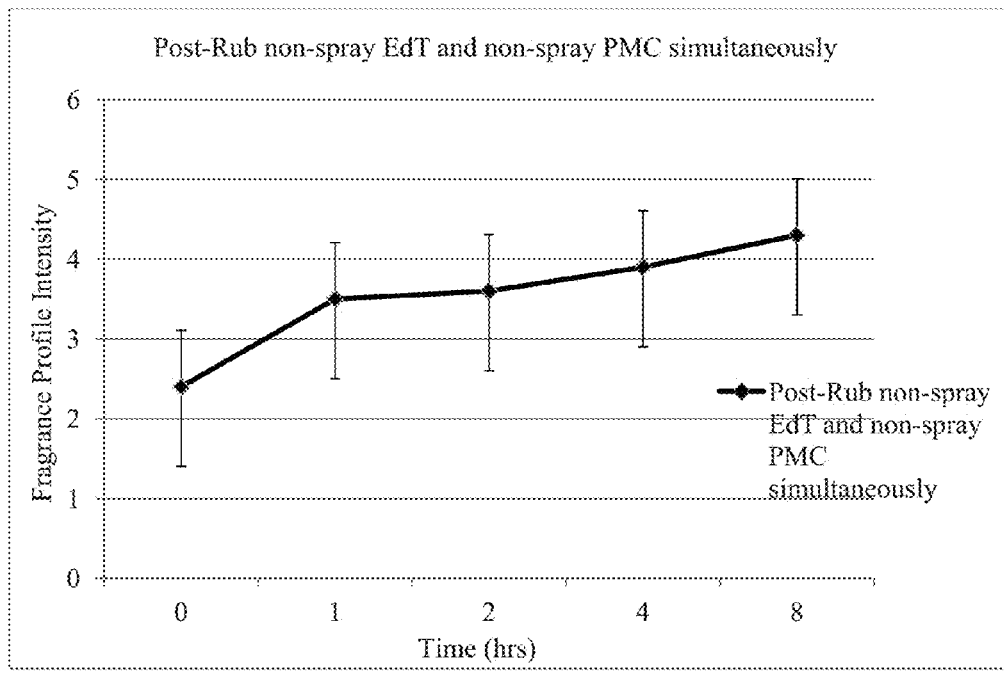
FIG. 4b shows the panel test results of perceived fragrance intensity profile of a volatile solvent based composition via non-spray dispenser and an aqueous based composition via non-spray dispenser simultaneously, as compared to a control, and as a function of time elapsed since application post-rubbing.

FIGS. 4a and 4b shows the fragrance intensity profile of the Spray EdT and Non-Spray PMC pre- and post-rubbing, respectively, as evaluated by 10 panelists. The perceived fragrance intensity profile of the Spray EdT and Non-Spray PMC is statistically greater than EdT alone control over eight hours, when the PMC is activated by rubbing. The fragrance intensity profile data generated pre-rubbing and without PMC activation shows no significant statistical difference versus EdT alone control over eight hours. The results demonstrate that the increased total amount of the fragrance material alone does not significantly impact the fragrance intensity assessment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A portable multi-fragrance compositional dispensing system comprising at least an aqueous based composition and a volatile solvent based composition, wherein the system comprises at least two separate containers, wherein:
   (a) a first container that contains the aqueous based composition, and a first dispenser operably connected to the first container and incorporating a first exit orifice, wherein the first dispenser is in fluid communication with the contained aqueous based composition and is a spray dispenser or a non-spray dispenser, and wherein the aqueous based composition comprises from about 0.1 wt % to about 95 wt % of water and from about 0.01 wt % to about 50 wt % of a plurality of microcapsules, wherein the wt % is by weight of the total aqueous based composition; and
   (b) a second container that contains the volatile solvent based composition, and a second dispenser operably connected to the second container and incorporating a second exit orifice, wherein the second dispenser is in fluid communication with the contained volatile solvent based composition and is a spray dispenser or a non-spray dispenser, and wherein the volatile solvent based composition comprises from about 0.01 wt % to about 98 wt % of a volatile solvent and from about 0.01 wt % to about 30 wt % of a first fragrance material, wherein the wt % is by weight of the total volatile solvent based composition.

2. The portable multi-fragrance compositional dispensing system according to claim 1, wherein:
   (i) the first dispenser is a spray dispenser and the second dispenser is a non-spray dispenser; or
   (ii) the first dispenser is a non-spray dispenser and the second dispenser is a spray dispenser; or
   (iii) the first dispenser is a non-spray dispenser and the second dispenser is a non-spray dispenser.

3. The portable multi-fragrance compositional dispensing system according to claim 1, with the proviso that both the first dispenser and the second dispenser cannot be spray dispensers.

4. The multi-component fragrance dispensing apparatus according to claim 1, wherein each of the spray dispensers, if present, is independently selected from: a propellant-driven dispenser; a mechanical spray finger-operated piston pump dispenser; a trigger-actuated piston-pump dispenser; other mechanical or electromechanical pump systems; a piezo-electric spray dispenser; an electrostatic spray dispenser; a bag-in-can or bottle system (pressurised or not) dispenser; an airless pump dispenser; or combinations thereof.

5. The multi-component fragrance dispensing apparatus according to claim 1, wherein each of the non-spray dispensers is independently selected from: a propellant-driven dispenser; a propellant-driven dispenser including a foaming nozzle; a roll-on dispenser; a dropper; a dauber dispenser; a pen dispenser; a brush dispenser; a stick dispenser; a pipette dispenser; a direct application dispenser; a pump (including finger, trigger, and airless pumps); a bag in can or bottle system (pressurised or not) dispenser; a mechanical/electromechanical dispenser; or combinations thereof.

6. The portable multi-fragrance compositional dispensing system according to claim 1, wherein the microcapsules comprise a core material and a shell that surrounds the core material, wherein the shell comprises a material selected from the group consisting of: polyacrylates; polyethylenes; polyamides; polystyrenes; polyisoprenes; polycarbonates; polyesters; polyureas; polyurethanes; polyolefins; polysaccharides; epoxy resins; vinyl polymers; urea cross-linked with formaldehyde or glutaraldehyde; melamine cross-linked with formaldehyde; gelatin-polyphosphate coacervates optionally cross-linked with glutaraldehyde; gelatin-gum Arabic coacervates; cross-linked silicone fluids; polyamine reacted with polyisocyanates; acrylate monomers polymerized via free radical polymerization; silk; wool; gelatin; cellulose; proteins; and combinations thereof.

7. The portable multi-fragrance compositional dispensing system according to claim 6, wherein the microcapsules comprise an oil soluble material that is selected from the group consisting of: mono-, di- and tri-esters of $C_4$-$C_{24}$ fatty acids and glycerine; isopropyl myristate; soybean oil; hexadecanoic acid; methyl ester; isododecane; and combinations thereof.

8. The portable multi-fragrance compositional dispensing system according to claim 1, wherein the microcapsules have a volume weighted fracture strength of from 0.1 MPa to 25 MPa.

9. The portable multi-fragrance compositional dispensing system according to claim 1, wherein the microcapsules have a median volume-weighted particle size of from 2 microns to 80 microns.

10. The portable multi-fragrance compositional dispensing system according to claim 1, wherein the aqueous based composition further comprises a second fragrance material encapsulated within the microcapsules.

11. The portable multi-fragrance compositional dispensing system according to claim 1, wherein the aqueous based composition is essentially free of a material selected from the group consisting of: a propellant; ethanol; a detersive surfactant; and combinations thereof.

12. The portable multi-fragrance compositional dispensing system according to claim 1, wherein the volatile solvent based composition is a sprayable liquid, and the aqueous based composition is a formulation selected from: mousses; gels; solids; creams; lotions; ointments; solutions; emulsions; films; and combinations thereof.

13. The portable multi-fragrance compositional dispensing system according to claim 1, wherein the volatile solvent is a branch or unbranched $C_1$ to $C_{10}$ alkanyl, alkenyl or alkynyl having at least one alcohol moiety.

14. A method of providing a longer lasting fragrance, the method comprising:
   (a) providing a portable multi-fragrance compositional dispensing system according to claim 1;
   (b) dispensing a dose of an aqueous based composition to a situs; and
   (c) dispensing a dose of a volatile solvent based composition to the situs;
      wherein the aqueous based composition and the volatile solvent based composition are dispensed simultaneously or sequentially, in either order.

* * * * *